(12) United States Patent
Kaern et al.

(10) Patent No.: US 7,837,661 B2
(45) Date of Patent: Nov. 23, 2010

(54) DEVICE FOR PROVIDING ANTI-REFLUX IN A BODY FLUID COLLECTION AND/OR SAMPLING SYSTEM, AND METHOD OF MANUFACTURING SUCH A DEVICE

(75) Inventors: Viggo Aaberg Kaern, Frederiksberg (DK); Andrew Edward Jenkins, South Wales (GB)

(73) Assignee: Coloplast A/S, Humlebaek (DK)

( * ) Notice: Subject to any disclaimer, the term of this patent is extended or adjusted under 35 U.S.C. 154(b) by 517 days.

(21) Appl. No.: 10/579,770

(22) PCT Filed: Nov. 19, 2004

(86) PCT No.: PCT/DK2004/000802

§ 371 (c)(1),
(2), (4) Date: Mar. 12, 2007

(87) PCT Pub. No.: WO2005/048890

PCT Pub. Date: Jun. 2, 2005

(65) Prior Publication Data

US 2007/0282283 A1  Dec. 6, 2007

(30) Foreign Application Priority Data

Nov. 19, 2003  (DK) ............................... 2003 01715

(51) Int. Cl.
*A61M 1/00* (2006.01)
(52) U.S. Cl. .................. 604/323; 604/326; 222/212; 222/491; 222/494
(58) Field of Classification Search .............. 604/323, 604/326
See application file for complete search history.

(56) References Cited

U.S. PATENT DOCUMENTS

| 3,529,599 | A |   | 9/1970  | Folkman et al. |
|-----------|---|---|---------|----------------|
| 3,586,041 | A |   | 6/1971  | Monestere |
| 3,807,444 | A | * | 4/1974  | Fortune ................... 137/512.1 |
| 3,901,235 | A |   | 8/1975  | Patel et al. |
| 3,965,900 | A | * | 6/1976  | Boedecker .................. 604/323 |
| 3,968,925 | A |   | 7/1976  | Johnston et al. |
| 4,784,654 | A | * | 11/1988 | Beecher ...................... 604/329 |
| 4,784,657 | A |   | 11/1988 | Shimp et al. |
| 4,795,449 | A |   | 1/1989  | Schneider et al. |
| 4,946,451 | A |   | 8/1990  | Cianci |
| 5,027,754 | A | * | 7/1991  | Morone ................. 123/184.54 |
| 5,117,871 | A | * | 6/1992  | Gardner et al. .............. 137/855 |
| 5,472,123 | A | * | 12/1995 | Jangaard ..................... 222/212 |
| 5,613,663 | A |   | 3/1997  | Schmidt et al. |

FOREIGN PATENT DOCUMENTS

| EP | 0 638 328 A1 | 2/1995 |
| GB | 2 130 097 A  | 5/1984 |
| GB | 2 313 430 A  | 11/1997 |

* cited by examiner

*Primary Examiner*—Tatyana Zalukaeva
*Assistant Examiner*—Ilya Y Treyger
(74) *Attorney, Agent, or Firm*—Coloplast Corp.; Daniel G. Chapik; Nicholas R. Baumann (57) ABSTRACT

The device (1) for providing anti-reflux has a valve element (9) formed from a sheet-shaped material blank. The valve element includes a connecting portion and a flap portion. Retaining means (10a,10b) for retaining the valve element are integral with the device. The connecting portion includes engagement means formed integrally with the valve element for engagement with the retaining means, the valve element projecting a coherent plane.

12 Claims, 9 Drawing Sheets

DEVICE FOR PROVIDING ANTI-REFLUX IN A BODY FLUID COLLECTION AND/OR SAMPLING SYSTEM, AND METHOD OF MANUFACTURING SUCH A DEVICE

This is a nationalization of PCT/DK04/000802 filed Nov. 19, 2004 and published in English.

BACKGROUND OF THE INVENTION

1. Field of the Invention

The present invention relates to a device for providing anti-reflux in a body fluid drainage and/or sampling system comprising at least one part providing a valve seat, and a valve element defining an outer contour formed from a sheet-shaped material blank, said valve element including at least one connecting portion and a flap portion and defining a longitudinal direction extending between the connecting portion and the flap portion, and retaining means for retaining the valve element with respect to the device, said retaining means being integral with the device.

2. Description of the Related Art

Devices for preventing backflow or reflux in systems for drainage and/or sampling of body fluids are well known in the art. Such devices, which either constitute or have the function of valves, may e.g. be positioned in a connector member connecting a urinary catheter with a urine drainage bag and prevent reflux of the collected urine to the catheter.

There are various designs of such devices. One type of valve which has proven efficient and which is at the same time of a simple structure is the flap or flutter type of valve. In such a valve, a relatively thin flap serves as a valve element and is connected with one or more parts of the device in such a way that the flap is able to flex or pivot between an open and a closed position. In the closed position, the flap abuts against a valve seat formed on any of the parts of the system. The flap thus allows for passage of fluid in one direction and seals against the valve seat when fluid pressure is exerted in the opposite direction.

The connection between the valve element and the other part or parts of the device may be carried out in different ways. One example is shown in GB patent application No. 2 313 430, in which a flap is formed as the inner portion of a hollow tubular structure forming a valve element. The flap of the valve element is connected integrally with a surrounding connecting portion at one point only and is thus separated from the connecting portion by a C-shaped slot. A simpler version of the same principle is disclosed in U.S. Pat. No. 3,529,599, in which the valve includes a disk-shaped valve element with a corresponding C-shaped slot. During manufacture of such a valve element, great care must be observed during provision of the slot, as the cut-out material produced may interfere with the manufacturing process and may, at worst, cause complete shutdown, just as any residual material on the cutting surface may affect the sealing properties of the valve. Furthermore, in order to obtain a correct seal, the valve seat of both of the above devices must extend radially inwards of the flap portion. Consequently, the overall dimensions of the anti-reflux device are necessarily relatively large in relation to the available inner dimensions of the tubes of the system.

U.S. Pat. No. 3,901,235 discloses an anti-reflux device positioned at the drip chamber of a body fluid collection bag, in which the valve element is relatively large and is sealed to the drip chamber around a major part of its periphery, leaving only the lower periphery free to pivot and allow for passage of fluid. However, as the flap portion thus only constitutes a small part of the valve element, there is a large amount of surplus material that does not take part in the actual function of the device. Furthermore, the sealing operation entails that the manufacture of the device becomes more complicated.

U.S. Pat. No. 3,968,925 discloses an anti-reflux valve located at the drip chamber of a fluid drainage bag, in which connecting portions of the valve element are formed as two radially extending ears protruding from the flap portion. The ears are received in retaining pockets formed under a separate retaining member in the form of a strip bonded to the drip chamber forming the valve seat. As the strip is only bonded to the drip chamber at selected portions, the valve element is slidably received in the pockets. In addition to the fact that such a slidable and thus immediately releasable connection is not desirable for all purposes, the manufacture and assembly of such a device is rendered expensive and cumbersome by the separate retaining member, its attachment to the drip chamber and the positioning of the valve element.

Furthermore, a commercially available device is known in which the valve element has the shape of a substantially cylindrical flap portion and a connecting portion, in which two apertures are formed for the accommodation of retaining means in the form of protrusions such as upstanding pins or the like. The valve elements including the apertures are usually formed by any suitable cutting operation, such as punching, of a blank of material. Due to the characteristics of the materials traditionally used in such valve elements and to the dimensions of the devices, difficulties may arise during manufacture of the valve elements. Such difficulties include that the cut-out or punched-out material in the form of free waste corresponding to the apertures may adhere to the valve elements due to static electricity generated by the handling of the material. In addition to the fact that the free waste may complicate the manufacturing process and the assembly of the device and render the valve leaking, it may have severe consequences if such free waste tears itself loose during use of the system and moves to other parts of the body fluid drainage and/or sampling system. Consequently, precautions in the form of an additional production step must be taken in order to secure that the free waste is removed during manufacture of the device.

SUMMARY OF THE INVENTION

With this background it is an object of the present invention to improve a device of the kind mentioned in the introduction with respect to ease and efficiency of manufacture, and which at the same time provides for a secure retention of the valve element in the device.

This and further objects are met by the provision of a device of the kind mentioned in the introduction, which is characterized in that the connecting portion includes engagement means formed integrally with the valve element for engagement with said retaining means, the valve element projecting a coherent plane. In this relation the term 'coherent' means that no material has been stamped, punched or cut out, i.e. no material has been removed from within the outer contour of the valve element. Slits may be provided within said outer contour, as long as no material is removed from the valve element.

The invention provides a device of the kind mentioned in the introduction, which is characterized in that the connecting portion includes engagement means formed integrally with the valve element for engagement with said retaining means, the sheet-shaped material being intact in said valve element.

The provision of integral engagement means in the valve element, which leave the material intact, entails that the disadvantages connected with the free waste produced during manufacture of the prior art devices are eliminated, both during the manufacturing process and in the finished product.

In a preferred embodiment, the engagement means include at least one incision and preferably two incisions in said outer contour, said incision or incisions extending substantially transverse with respect to said longitudinal direction, said incision or incisions being preferably formed at the transition between the flap portion and the connecting portion. This provides for a reliable connection between the valve element and the retaining means of the device, and an optimum use of the material and at the same time, the dimensions of the flap portion and the connecting portion may be chosen in an advantageous manner.

In order to improve the retention of the valve element with respect to the retaining means even further, the engagement means may include a hook-shaped section positioned outwards of said at least one incision with respect to said longitudinal direction.

In an embodiment, which is particularly advantageous with respect to manufacturing conditions, the outer contour forms a curve defining a continuously advancing function on a respective side of the longitudinal direction.

In an alternative embodiment, the engagement means are formed within said outer contour. This provides for a particularly compact design of the valve element.

The engagement means are advantageously provided as at least one slit in the sheet-shaped material.

In one embodiment of the invention the engagement means are formed integrally in said outer contour.

The body fluid to be collected and/or sampled may be of any conceivable kind. However, the device is particularly advantageous for applications in which the body fluid is urine.

In one embodiment of the invention the valve seat providing part constitutes a connector for connection with a urinary catheter, forms part of a hose in said system or of a sample port device.

One embodiment of the invention relates to a valve element including at least one connecting portion and a flap portion and defining a longitudinal direction extending between the connecting portion and the flap portion, and with engagement means integrally formed in the valve element, wherein the valve element including the engagement means is manufactured by cutting along a closed line in a sheet-shaped material blank.

One embodiment relates to a method of manufacturing a device for providing anti-reflux in a body fluid drainage and/or sampling system, comprising providing at least one part including a valve seat, forming a valve element defining an outer contour from a sheet-shaped material blank, said valve element including at least one connecting portion and a flap portion, providing retaining means integral with the device, and bringing the connecting portion into engagement with the retaining means, wherein engagement means are formed integrally with the valve element, the valve element projecting a coherent plane.

One embodiment of the invention relates to a method of manufacturing a valve element in a body fluid drainage and or sampling system having a connection portion, a flap portion, and engagement means integrally in the valve element comprising the step of cutting the valve element and the engagement means along one closed line in a sheet-shaped material blank.

One embodiment relates to a method of manufacturing a valve element in a body fluid drainage and or sampling system having a connection portion, a flap portion, and engagement means integrally in the valve element comprising the step of cutting the valve element along one closed line in a sheet-shaped material blank; and cutting at least one slit in the sheet-shaped material leaving no waste material.

Although many of the embodiments have a connection portion, which is symmetrical around a horizontal axis, it will readily be appreciated that the upper and the lower part of the connection portion can have different profiles.

As is well known by the skilled person, the cutting operation may be performed by punching, stamping or die-cutting, preferably in a rolling operation, or by using any other suitable technique such as cutting by water or laser.

Further details and advantages are readily appreciated from the appended drawings and the following description.

BRIEF DESCRIPTION OF THE DRAWINGS

In the following the invention will be described in further detail with reference to the schematic drawings, in which like references are used for like elements, and in which.

DETAILED DESCRIPTION OF THE PRESENT INVENTION

The object of the invention provides two different principles for movement of the valve element, namely one where the valve element is fixed in the flow direction at the connecting portion, which calls for the valve element to flex to allow the valve to function properly, and the other where the valve element has some clearance in the flow direction so as to allow the valve element to pivot freely around the retaining means, the latter principle not necessarily requiring any flexibility of the material of the valve element. The two principles may also be combined. Thus, the sheet-shaped material forming the blank can be chosen with regard to the applied principle(s) of movement.

In one aspect of the invention the contact surface, between the connection portion of the valve element and the retaining means is minimized, thereby reducing the friction, enabling the valve element to pivot more freely around the retaining means.

In another aspect of the invention the clearance between the connection portion of the valve element and the retaining means is minimized, providing the possibility of maximum control of the valve element regarding movement in the plane, in which the valve element extends, e.g. lateral movement.

In yet another aspect of the invention the retaining means are in the shape of pins. This will entail an improved flow through the valve, as cavities making up dead spots created by integral retaining means in the shape of integrated walls are eliminated. These dead spots impeding the free flow of the fluid are especially undesirably, since they increase the risk of bacterial growth and other possible accumulation of material in the system.

DESCRIPTION OF THE PREFERRED EMBODIMENTS

The invention is now explained more in detail with reference to the drawings showing preferred embodiments of the invention.

Figure 1:
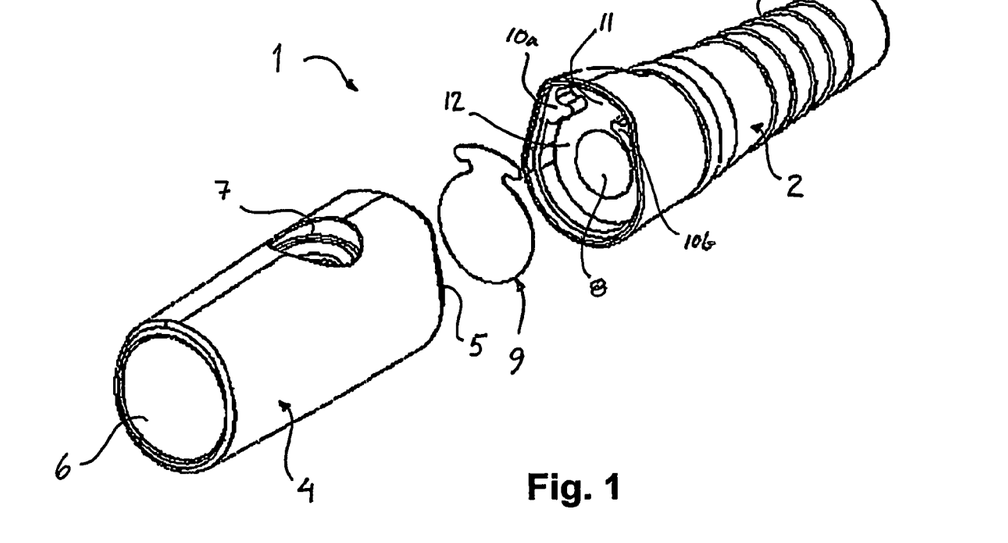
FIG. 1 shows an exploded perspective view of a device according to an embodiment of the invention.

A device for providing anti-reflux, i.e. for preventing backflow or reflux, in a body fluid drainage and/or sampling system is generally designated 1 in FIG. 1. The device 1 comprises a first part 2, which in the embodiment shown constitutes a connector having connecting means 3 for releasable interconnection with e.g. a discharge tube (not shown) of a urinary catheter, and a second part 4 intended for connection with the first part 2 at one end 5. At an opposite end 6 of the second part 4 connecting means (not shown in detail) are provided for connection with e.g. a tube or hose (not shown) leading to e.g. a collection bag for the body fluid. The second part 4 furthermore comprises an opening 7 for the taking of a sample of the fluid. The above details of the device are not essential to the present invention. The device could be positioned in other parts of the system as well. Examples of such alternative positions are: in a hose or tube member of the system, or in a sample port device. The device may also be utilized in connection with other body fluids than urine, but also in connection with other fluids as well as gasses.

The first part 2 and the second part 4 each has a throughgoing cavity, of which only the cavity 8 of the first part 4 is clearly visible. The cavities are intended to lead the body fluid from e.g. the catheter to the collection bag. In order to prevent body fluid from flowing in the opposite direction, a valve element 9 is inserted between the first and second parts 2,4. The valve element 9, which will be described in further detail in the following, is accommodated in the first part 2 and is retained in its position by means of integral retaining means. The integral retaining means include two protrusions 10a,10b formed integrally with the inner wall of the first part 2. These protrusions 10a,10b split the space in which the valve element 9 is accommodated partly in two, i.e. a recess 11 on one side and a section forming a valve seat 12 on the other. The second part 4 may be provided with one or more protrusions corresponding to the recess 11 such that the valve element 8 is securely retained in the first part 2. In case fluid for some reason should flow or be pressed back in the direction from the second part 4 to the first part 2, the valve element 9 is brought into abutment with the valve seat 12 surrounding the cavity 8, and backflow into the first part 2 and further into e.g. the catheter is prevented.

Figure 2:
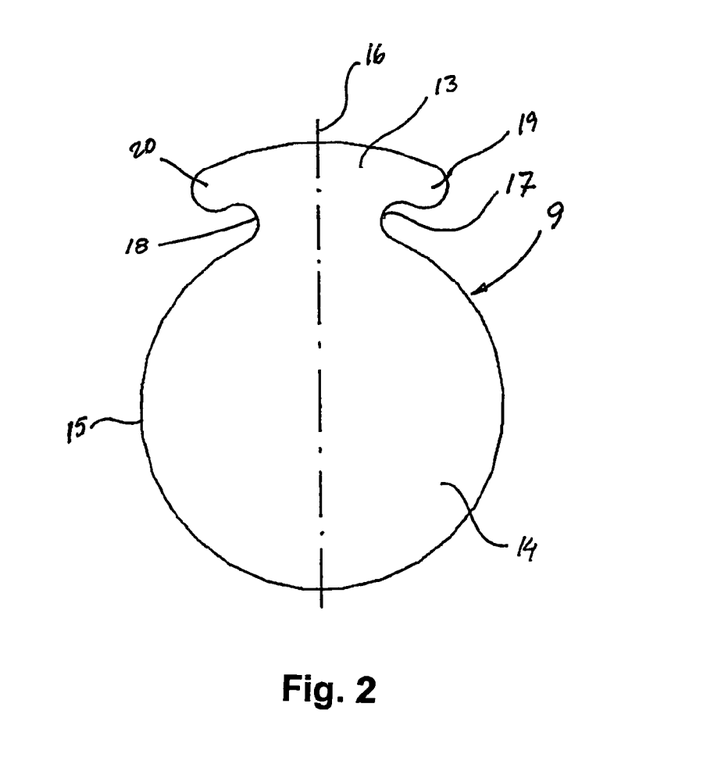
FIG. 2 shows a plan view, on a larger scale, of a detail of the device shown in FIG. 1, FIGS. 3 to 22 show plan views of alternative embodiments of a detail of the device according to the invention.

The structure of the valve element 9 is shown in further detail in FIG. 2. The valve element 9 includes a connecting portion 13 and a flap portion 14. In the embodiment of FIGS. 1 and 2, the shape of the valve element 9 as defined by its outer contour 15 and a longitudinal direction illustrated by a longitudinal line 16 is such that an incision 17,18 is formed at the transition between the flap portion 14 and the connecting portion 13 on either side of the longitudinal line 16. Each of the incisions 17,18 extends substantially transverse with respect to the longitudinal direction of the valve element 9, however as indicated in FIG. 2 with a slight inclination in the direction of the connecting portion 13. Outwards of the incisions 17,18, as seen with respect to the longitudinal line 16, a hook-shaped section 19,20 is formed on the connecting portion 13. The incisions 17,18 and the hook-shaped portions 19,20 form part of integral engagement means of the valve element 9. As will be described in further detail in connection with the description of the embodiment of FIG. 3, the provision of integral engagement means entails a number of advantages during manufacture as well as in use of the device. During manufacture of the device these integral engagement means are brought into engagement with the retaining means of the first part 2, as the connecting portion 13 of the valve element 9 is placed in the recess 11. The form-locking engagement between the incisions 17,18 and the hook-shaped sections 19,20 of the valve element 9 and the protrusions 10a, 10b of the first part 2 prevents that the valve element 9 is moved from its accommodation in the first part 2.

It is noted that in the embodiment shown, the valve element 9 is substantially symmetrical with respect to the longitudinal line 16. However, other configurations of the valve element 9 are of course conceivable, including those in which the incisions are not of the same shape. Furthermore, the first part 2 and the second part 4 may be separate parts which are assembled in any suitable manner. The device 1 may comprise additional parts such as e.g. separate locking means for keeping the first and second parts 2,4 in an assembled state.

Figures 3, 4, 5:
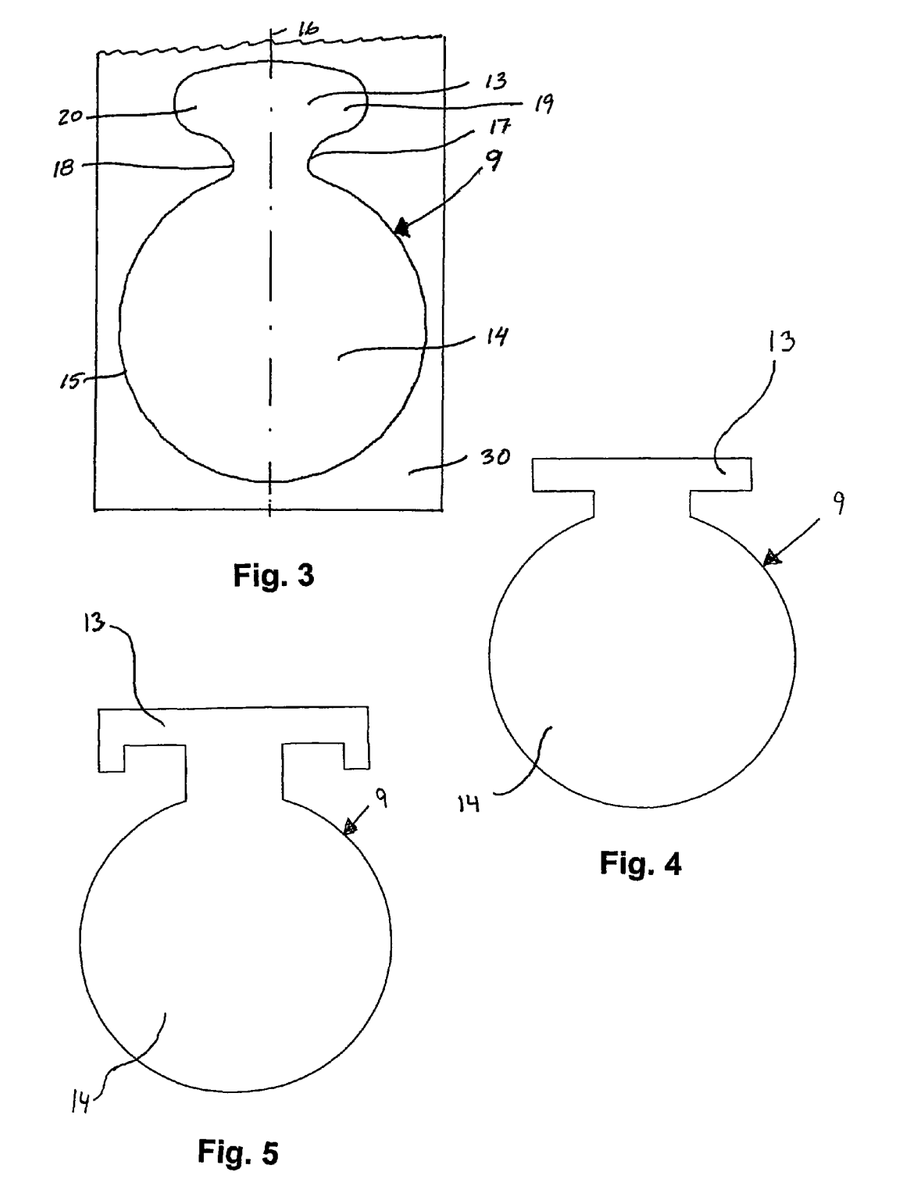

In FIG. 3 another embodiment of a valve element 9 is shown. Only differences from the embodiment shown in FIGS. 1 and 2 will be described in detail. The valve element 9 comprises a connecting portion 13 and a flap portion 14. In principle, the engagement means of the valve element 9 are formed in the same manner as in the embodiment of FIGS. 1 and 2 and thus include incisions 17,18 for engagement with retaining means of e.g. the first part of the anti-reflux device. However, sections 19,20 of the connecting portion 13 do not extend outwards of the incisions 17,18, as the outer contour 15 of the valve element 9 forms a curve defining a continuously advancing function on a respective side of the longitudinal direction illustrated by longitudinal line 16. This entails, i.a., that during manufacture of the valve element 9, only two points at a time need to be cut when the valve element 9 is cut out of a blank of sheet-shaped material 30. The cutting operation may be performed by punching, stamping or die-cutting, preferably in a rolling operation, or by using any other suitable technique such as cutting by water or laser.

A further embodiment of the valve element 9 is shown in FIG. 4, where the connection portion 13 is substantially rectangular.

FIG. 5 shows an embodiment of the valve element 9, where the main portion of the connection portion 13 is substantially rectangular with hook-shaped parts on both ends of the connection portion 13.

Figure 6:
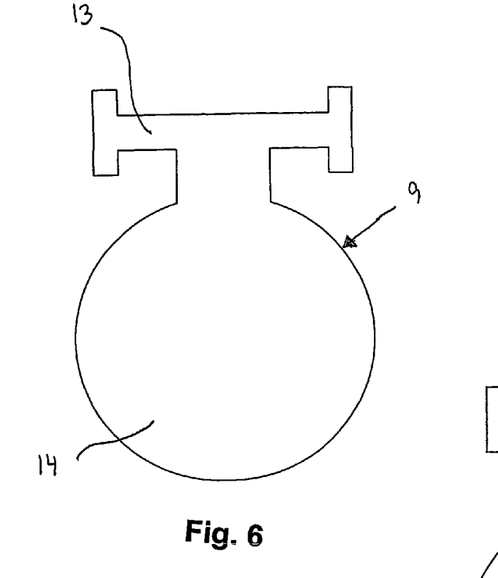

In FIG. 6 the connection portion 13 has a similar profile as in FIG. 5, only this one is symmetrical around a horizontal axis. As the anti-reflux device can be in various positions during use, e.g. turned upside down, the connecting portion 13 may be substantially symmetrical around a horizontal axis to achieve similar contact surfaces with the retaining means corresponding to the protrusions 10a, 10b in FIG. 1 regardless of the orientation of the anti-reflux device. It is preferable that the retaining means of the anti-reflux device, e.g. provided in the first part, are formed in a corresponding manner.

Figure 7:
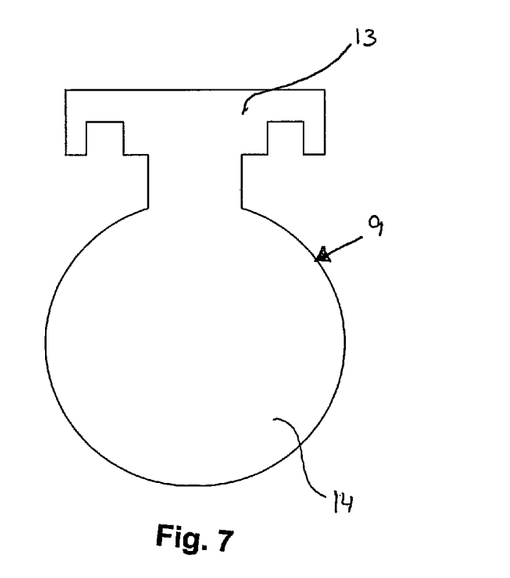

FIG. 7 shows another embodiment of the valve element 9, where the connection portion 13 is substantially rectangular, but with incisions in the lower part of the connection portion 13.

Figure 8:
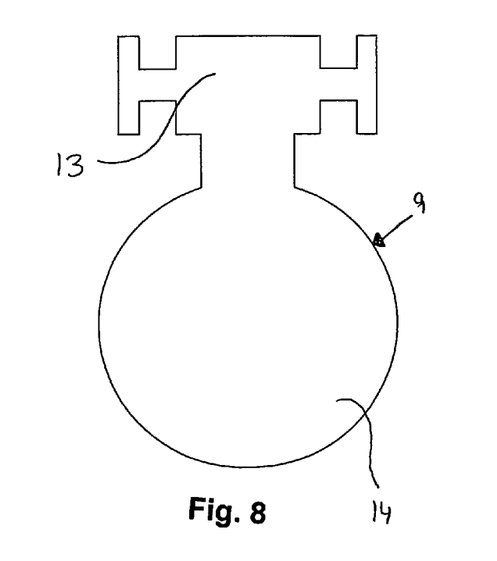

The embodiment of the valve element 9 shown in FIG. 8 has a similar profile as the valve element in FIG. 7, only this one is symmetrical around a horizontal axis. This shape of the connection portion 13 as well as the one of FIG. 8 provides the possibility of maximum control of the valve element 9 regarding movement in the plane, in which the valve element extends, e.g. lateral movement.

Figures 9, 10, 11:
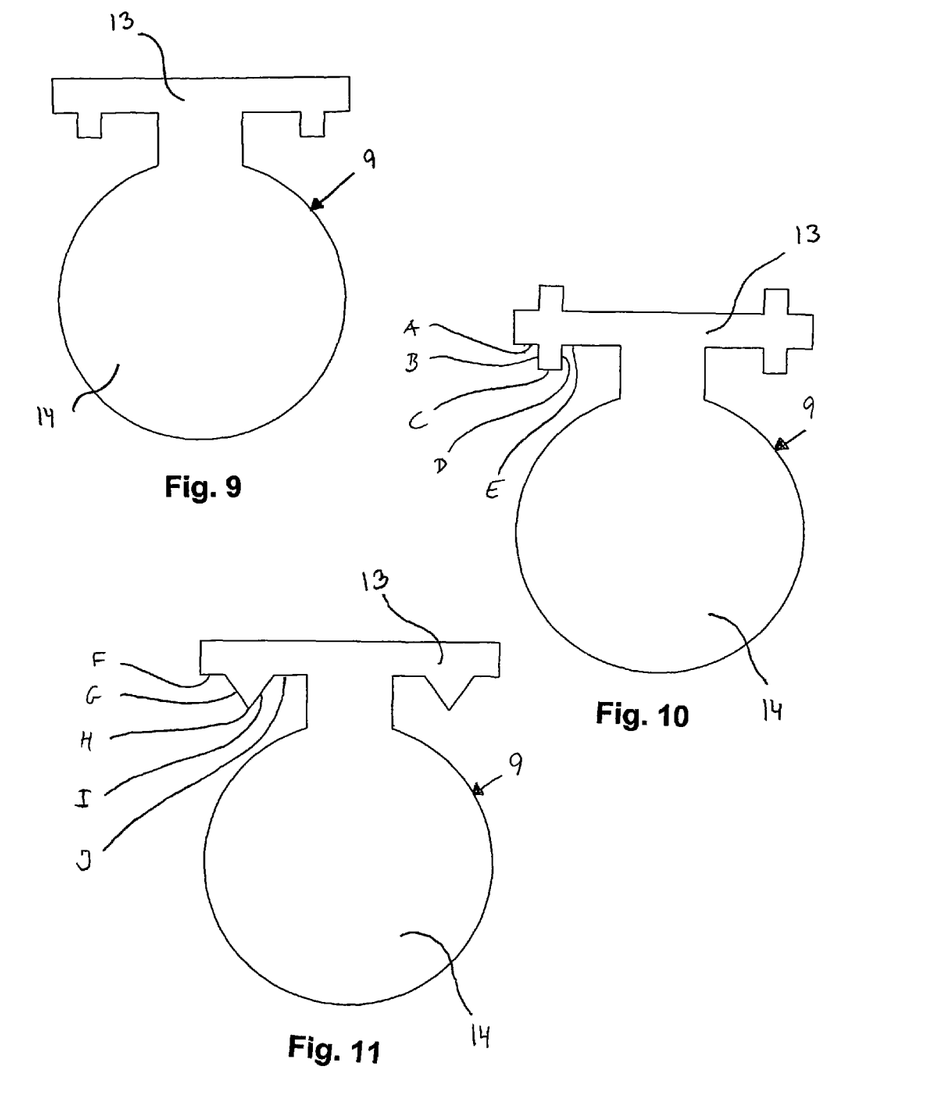

In FIG. 9 another embodiment of the valve element 9 is shown, where the main portion of the connection portion 13 is rectangular with downward projecting parts situated at some distance from the ends of the connection portion 13. This profile of the connection portion 13 provides the possibility of having relatively small contact surfaces with the retaining means, which enables the valve element 9 to pivot more freely around the retaining means.

The sheet-shaped material forming the blank 30 may be of any suitable material known per se and having suitable dimensions, such as a relatively thin plastic material. As in the previously and subsequently described embodiments, the provision of integral engagement means entails that no cut-out or punched-out material in the form of free waste is produced. There is thus no need for manufacturing steps including the removal of the free waste, as the lattice waste formed is coherent. This is of particular importance when the dimensions are small, as is the case here, as forces resulting i.a. from the static electricity generated by handling of the material may exceed other forces, such as gravity.

FIGS. 10 to 11 show further embodiments of the valve element 9. The connection portion 13 of the valve element 9 in FIG. 10 has a similar profile as the valve element in FIG. 9, only this one is symmetrical around a horizontal axis. Moreover, examples of contact surfaces A, B, C, D, E between the connection portion 13 and the retaining means (not shown) are indicated to illustrate the numerous contact surfaces possible. The different contact surfaces can be applied in combination. For the sake of simplicity the contact surfaces A, B, C, D, E are only indicated in one area of the connection portion 13, but the same options apply to the distal end as well as the upper part of the connection portion 13. FIG. 11 shows an embodiment of the valve element 9, where the main portion of the connection portion 13 is rectangular with downward projecting, substantially triangular parts. In FIG. 11 other examples of contact surfaces F, G, H, I, J are shown. It is preferable that the retaining means of the anti-reflux device, e.g. provided in the first part, are formed in a corresponding manner so as to accommodate the valve element 9 and the contact surfaces.

Figure 12:
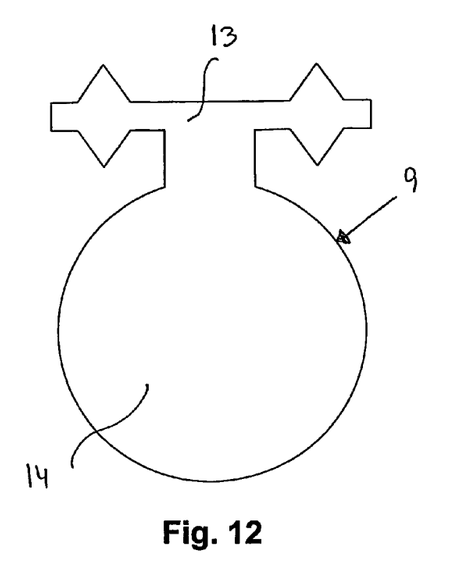

The embodiment of the valve element 9 shown in FIG. 12 has a similar profile as the valve element in FIG. 11, only this one is symmetrical around a horizontal axis.

Figure 13:
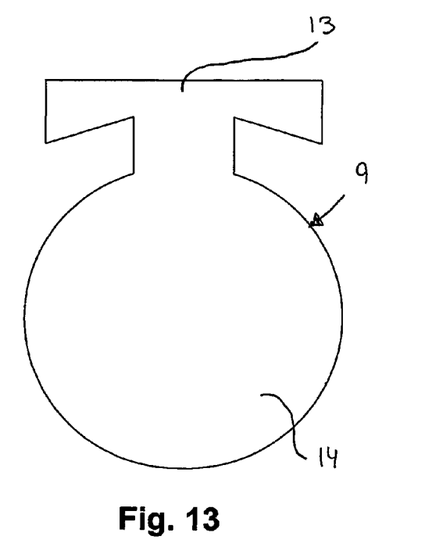

FIG. 13 shows an embodiment of the valve element 9, where the top and the sides of the connection portion 13 are substantially perpendicular, whereas the lower parts of the contour of the connection portion 13 are downward inclined towards the end of the connection portion 13.

Figure 14:
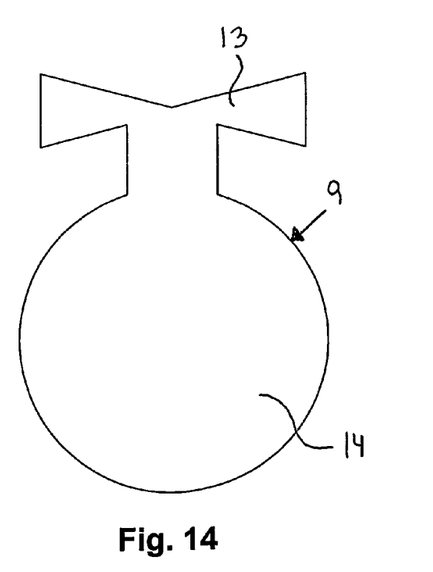

In FIG. 14 the connection portion 13 has a similar profile as in FIG. 13, only this one is symmetrical around a horizontal axis, i.e. the top of the connection portion 13 has downward inclined parts of the contour as well.

Figure 15:
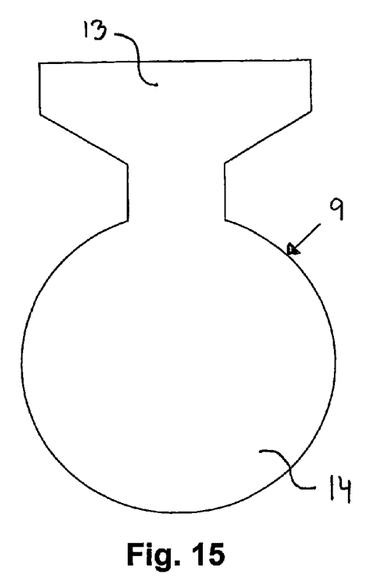

FIG. 15 shows an embodiment of the valve element 9, where the top and the sides of the connection portion 13 are substantially perpendicular, whereas the lower parts of the contour of the connection portion 13 are downward inclined towards the middle of the connection portion 13.

Figure 16:
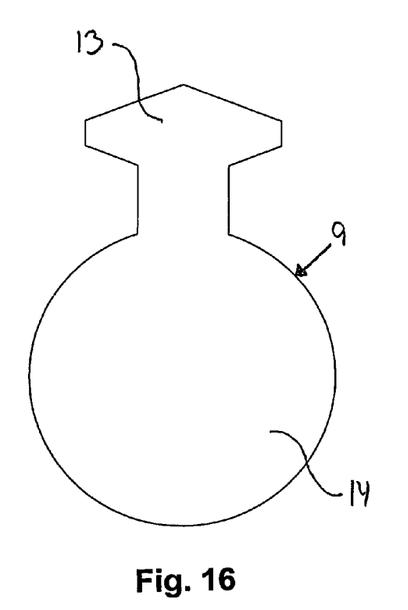

The embodiment of the valve element 9 shown in FIG. 16 has a similar profile as the valve element in FIG. 15, only this one is substantially symmetrical around a horizontal axis, i.e. the top of the connection portion 13 has downward inclined parts of the contour as well.

Figure 17:
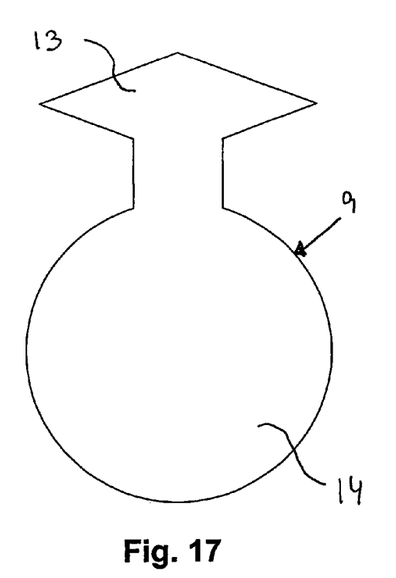

In FIG. 17 the embodiment of the valve element 9 has a connection portion 13, which is substantially trapezoidal.

Figure 18:
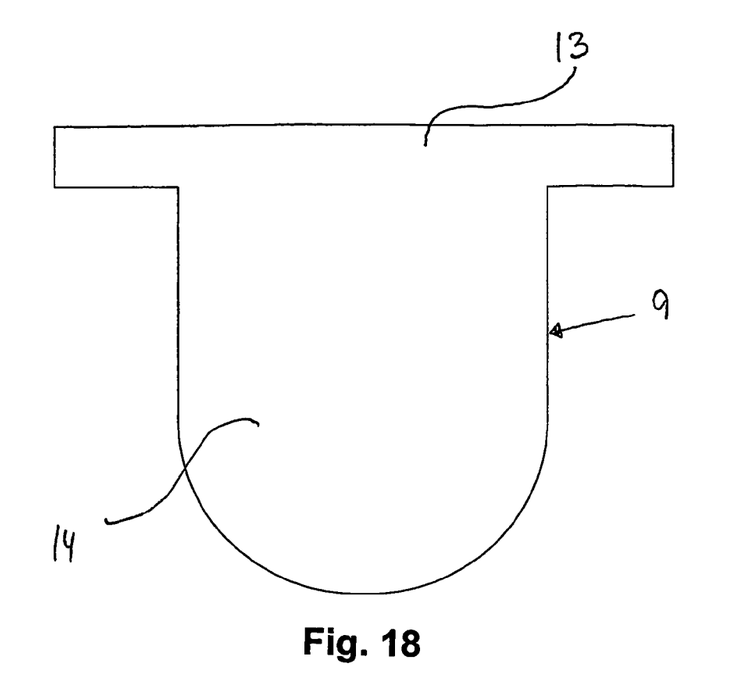

FIG. 18 shows an embodiment of the valve element 9, where the connection portion 13 is substantially rectangular, and where the flap portion 14 is in the shape of a crescent, which ends are connected to the connection portion 13 via straight lines.

Figure 19:
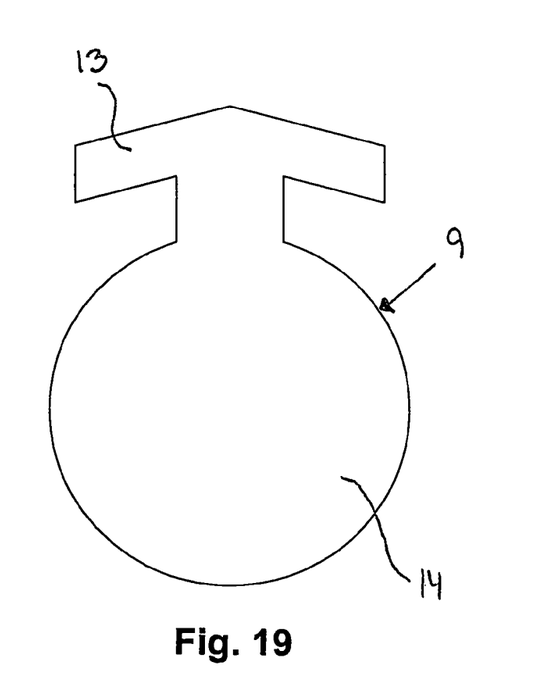

FIG. 19 shows an embodiment of the valve element 9, where the lower and the upper parts of the contour of the connection portion 13 are downward inclined towards the ends of the connection portion 13.

As an alternative, the engagement means may be provided within the outer contour of the valve element. It is, however, important that the sheet-shaped material is kept intact during the provision of the engagement means and thus projects a coherent plane. It is further preferable that the retaining means of the anti-reflux device, e.g. provided in the first part, are formed in a corresponding manner.

Figure 20:
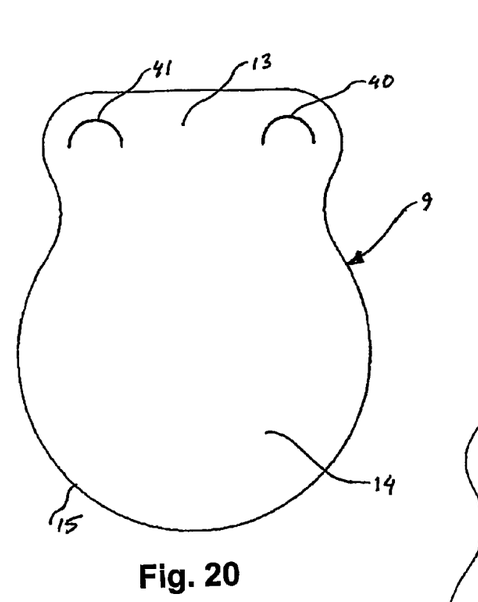
Figure 21:
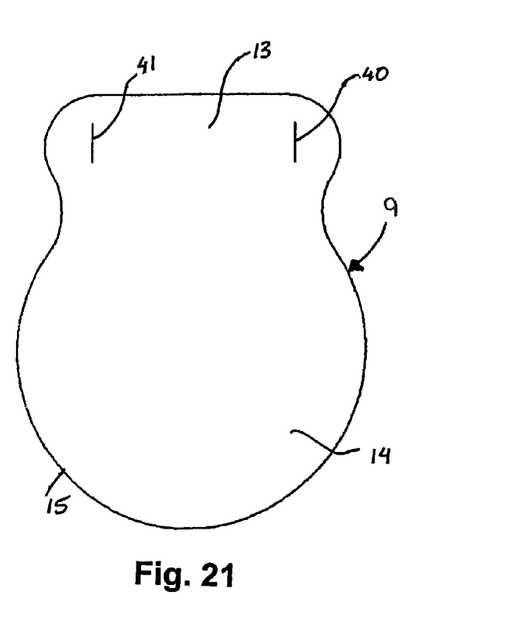
Figure 22:
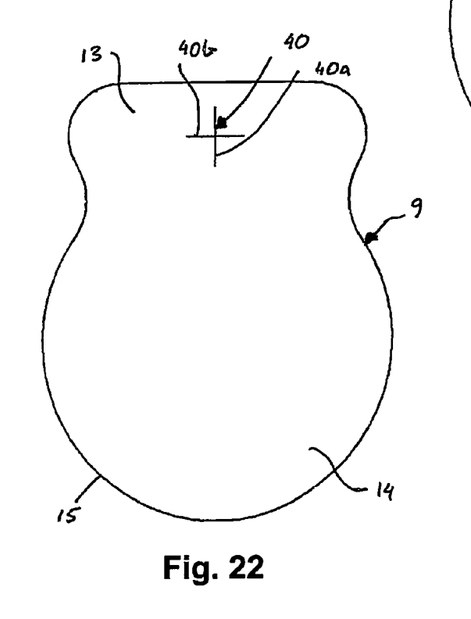

Examples of such engagement means are shown in FIGS. 20 to 22, in which only features regarding the engagement means will be described in detail.

In the embodiment of FIG. 20, the engagement means are formed as a pair of crescent-shaped slits 40 and 41 in the connecting portion 13 of the valve element 9. The outer contour 15 of the valve element 9 may be formed such that the transition area between the flap portion 14 and the connecting portion 13 is slightly narrowed.

In FIG. 21 a pair of longitudinally extending slits 40,41 constitute the engagement means.

In FIG. 22, only one set 40 of engagement means is provided in the form of two crossed slits 40a,40b. Other configurations and combinations of such slits are of course conceivable, including three sets of engagement means cooperating with a corresponding number of retaining means of the device.

Figure 23:
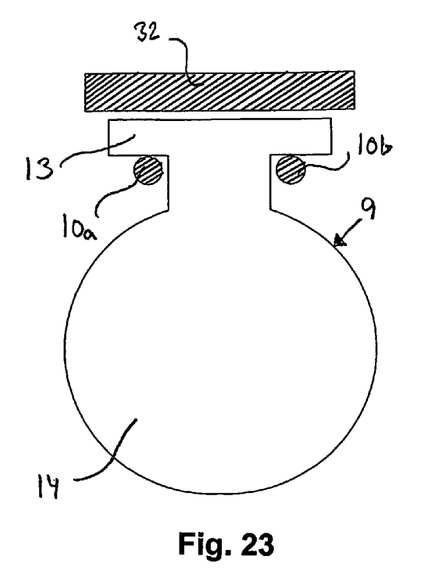
FIGS. 23 to 25 shows sectional views of details of the device according to the invention.

FIG. 23 shows an embodiment of the invention, where the retaining means 10a, 10b are two protrusions in the shape of pins which protrude from the back wall of the recess 11 (not shown). Upper retaining means 32 is also provided in the shape of a substantially flat surface, against which the valve element 9 can rest if for example the anti-reflux device is placed upside down.

Figure 24:
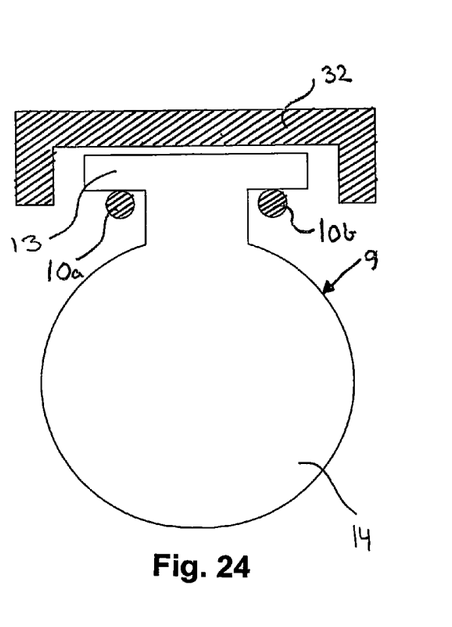
Figure 25:
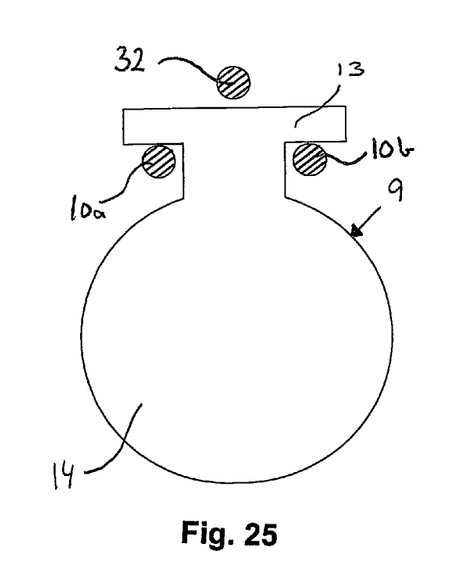

In FIG. 24 another embodiment of the invention is shown, in which the retaining means 10a, 10b are in the shape of pins, and the upper retaining means 32 is provided with downward projecting parts FIG. 25 shows yet another embodiment of the invention, in which the retaining means 10a, 10b as well as the upper retaining means 32 are in the shape of pins.

The appended drawings are schematic, i.e. they are schematic examples of embodiments of the invention. For example the shape of the flap portion 14 and/or the different angles of the connection portion 13 can be altered, or the corners can be rounded which will improve the functionality and hygiene of the device as corners are eliminated causing the urine to flow more freely.

The invention should not be regarded as being limited to the embodiments described in the above and shown in the drawings. Various modifications and combinations are conceivable without departing from the scope of the appended claims.

The invention claimed is:

1. A device for providing anti-reflux comprising: at least one part providing a valve seat, and a valve element defining an outer contour formed from a sheet-shaped material blank, said valve element including at least one connecting portion and a flap portion and defining a longitudinal direction extending between the connecting portion and the flap portion, and retaining means for retaining the valve element with respect to the device, said retaining means being integral with the device, the connecting portion including a hook-shaped engagement section formed integrally with the valve element for engagement with said retaining means, the valve element projecting a coherent plane.

2. A device according to claim 1, for providing anti-reflux in a body fluid drainage and/or sampling system.

3. A device according to claim 1, wherein the hook-shaped engagement section is formed from an incision in said outer contour, said incision extending substantially transverse with respect to said longitudinal direction at the transition between the flap portion and the connecting portion.

4. A device according to claim 3, wherein the hook-shaped engagement section is formed from two incisions.

5. A device for providing anti-reflux comprising: at least one part providing a valve seat, and a valve element defining an outer contour formed from a sheet-shaped material blank, said valve element including at least one connecting portion and a flap portion and defining a longitudinal direction extending between the connecting portion and the flap portion, and retaining means for retaining the valve element with respect to the device, said retaining means being integral with the device, characterized in that the connecting portion includes engagement means formed integrally with the valve element for engagement with said retaining means, the valve element projecting a coherent plane, wherein the engagement means include at least one incision, said at least one incision extending substantially transverse with respect to said longitudinal direction, said at least one incision being at the transition between the flap portion and the connecting portion and said engagement means include a hook-shaped section positioned outwards of said at least one incision with respect to said longitudinal direction.

6. A device according to claim 1, in which said outer contour forms a curve defining a continuously advancing function on a respective side of the longitudinal direction.

7. A device as claimed in claim 1, in which said hook-shaped engagement section is formed within said outer contour.

8. A device as claimed in claim 7, in which said engagement means are provided as at least one slit the sheet-shaped material.

9. A device according to claim 1, wherein said engagement means are formed integrally in said outer contour.

10. A device as claimed in claim 2, in which the body fluid is urine.

11. A device as claimed in claim 10, wherein said valve seat providing part constitutes a connector for connection with a urinary catheter, forms part of a hose in said system or of a sample port device.

12. A valve element including at least one connecting portion and a flap portion and defining a longitudinal direction extending between the connecting portion and the flap portion, the connecting portion including a hook-shaped engagement section integrally formed in the valve element, and the valve element projects a coherent plane.

* * * * *